(12) United States Patent
Tetzlaff et al.

(10) Patent No.: US 6,511,480 B1
(45) Date of Patent: *Jan. 28, 2003

(54) OPEN VESSEL SEALING FORCEPS WITH DISPOSABLE ELECTRODES (75) Inventors: Philip M. Tetzlaff, Golden, CO (US); Steven P. Buysse, Longmont, CO (US); Kate R. Dawes, Superior, CO (US); Dale F. Schmaltz, Fort Collins, CO (US); Randel A. Frazier, Louisville, CO (US); Michael J. Lands, Palm Harbor, FL (US); Steven W. Lukianow, Bouler, CO (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/425,696

(22) Filed: Oct. 22, 1999

Related U.S. Application Data (63) Continuation-in-part of application No. 09/177,950, filed on Oct. 23, 1998, now abandoned, and a continuation-in-part of application No. 09/178,027, filed on Oct. 23, 1998, now Pat. No. 6,277,117.

(51) Int. Cl.[7] ............................................. A61B 18/18
(52) U.S. Cl. ........................................... 606/51; 606/41
(58) Field of Search ........................ 606/41, 45, 48–52, 606/174, 205–208

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,176,479 A | 10/1939 | Willis |

(List continued on next page.)

FOREIGN PATENT DOCUMENTS

| CA | 2104423 | 2/1994 |
| EP | 518230 | 12/1992 |
| EP | 0 584 787 A1 | 3/1994 |
| EP | 0 853 922 A1 | 7/1998 |
| SU | 401367 | 11/1974 |
| WO | WO 0024330 | 5/2000 |

OTHER PUBLICATIONS

International Search Report—PCT/US98/18640.
International Search Report—PCT/US98/23950.
Sigel et al., "The Mechanism of Blood Vessel Closure by High Frequency Electrocoagulation".
Surgery Gynecology & Obstetrics, Oct. 1965 pp. 823–831.
Bergdahl et al. "Studies on Coagulation and the Development of An Automatic Computerized Bipolar Coagulator" J. Neurosurg, vol. 75 Jul. 1991, pp. 148–151.

Primary Examiner—Rosiland S. Kearney (57) ABSTRACT

A removable electrode assembly for use in combination with a forceps having opposing end effectors and a handle for effecting movement of the end effectors relative to one another. The electrode assembly includes a housing which is removably engageable with the forceps and a pair of electrodes which are attachable to a distal end of the housing. The electrodes are removably engageable with the end effectors of the forceps such that the electrodes reside in opposing relation relative to one another. The electrode assembly also includes a cover plate which is removably attachable to the housing and at least one stop member for controlling the distance the electrodes move relative to one another.

20 Claims, 10 Drawing Sheets

U.S. PATENT DOCUMENTS

| | | |
|---|---|---|
| 3,643,663 A | 2/1972 | Sutter |
| 3,651,811 A | 3/1972 | Hildebrandt et al. |
| 3,920,021 A | 11/1975 | Hiltebrandt |
| 3,938,527 A | 2/1976 | Rioux et al. |
| 3,952,749 A | 4/1976 | Fridolph et al. |
| 4,005,714 A | 2/1977 | Hiltebrandt |
| 4,370,980 A | 2/1983 | Lottick |
| 4,552,143 A | 11/1985 | Lottick |
| 4,597,379 A | 7/1986 | Kihn et al. |
| 4,671,274 A | 6/1987 | Sorochenko |
| 4,685,459 A | 8/1987 | Koch et al. |
| 4,887,612 A | 12/1989 | Esser et al. |
| 4,938,761 A | 7/1990 | Ensslin |
| 5,007,908 A | 4/1991 | Rydell |
| 5,026,370 A | 6/1991 | Lottick |
| 5,116,332 A | 5/1992 | Lottick |
| 5,151,102 A | 9/1992 | Kamiyama et al. |
| 5,197,964 A | 3/1993 | Parins |
| 5,215,101 A | 6/1993 | Jacobs et al. |
| 5,217,458 A | 6/1993 | Parins |
| 5,250,047 A | 10/1993 | Rydell |
| 5,258,006 A | 11/1993 | Rydell et al. |
| 5,277,201 A | 1/1994 | Stern |
| 5,282,799 A | 2/1994 | Rydell |
| 5,290,286 A | 3/1994 | Parins |
| 5,318,589 A | 6/1994 | Lichtman |
| 5,324,289 A | 6/1994 | Eggers |
| 5,330,471 A | 7/1994 | Eggers |
| 5,334,215 A | 8/1994 | Chen |
| 5,342,359 A | 8/1994 | Rydell |
| 5,342,381 A | 8/1994 | Tidemand |
| 5,352,222 A | 10/1994 | Rydell |
| 5,356,408 A | 10/1994 | Rydell |
| 5,389,104 A | 2/1995 | Hahnen et al. |
| 5,391,166 A | 2/1995 | Eggers |
| 5,403,312 A | 4/1995 | Yates et al. |
| 5,411,519 A | 5/1995 | Tovey et al. |
| 5,431,674 A | 7/1995 | Basile et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,456,684 A | 10/1995 | Schmidt et al. |
| 5,462,546 A | 10/1995 | Rydell |
| 5,472,443 A | 12/1995 | Cordis et al. |
| 5,478,351 A | 12/1995 | Meade et al. |
| 5,484,436 A | 1/1996 | Eggers et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,558,672 A | 9/1996 | Edwards et al. |
| 5,569,241 A | 10/1996 | Edwards |
| 5,573,535 A | 11/1996 | Viklund |
| 5,603,711 A | 2/1997 | Parins et al. |
| 5,626,578 A | 5/1997 | Tihon |
| 5,637,110 A | 6/1997 | Pennybacker et al. |
| 5,658,281 A | 8/1997 | Heard |
| 5,667,526 A | 9/1997 | Levin |
| 5,674,220 A | 10/1997 | Fox et al. |
| 5,693,051 A | 12/1997 | Schulze et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,743,906 A | 4/1998 | Parins et al. |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,800,449 A | 9/1998 | Wales |
| 5,810,808 A | 9/1998 | Eggers |
| 5,814,043 A | 9/1998 | Shapeton |
| 5,827,279 A | 10/1998 | Hughett et al. |
| 5,827,281 A | 10/1998 | Levin |
| 5,843,080 A | 12/1998 | Fleenor et al. |
| 5,891,141 A | 4/1999 | Rydell |
| 5,891,142 A | 4/1999 | Eggers et al. |
| 5,893,875 A | 4/1999 | O'Connor et al. |
| 5,902,301 A | 5/1999 | Olig |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,951,549 A | 9/1999 | Richardson et al. |
| 5,954,720 A | 9/1999 | Wilson et al. |
| 6,004,335 A | 12/1999 | Vaitekunas et al. |
| 6,039,733 A | 3/2000 | Buysse et al. |
| 6,053,914 A | 4/2000 | Eggers et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,099,550 A | 8/2000 | Yoon |
| 6,110,171 A | 8/2000 | Rydell |
| 6,113,596 A | 9/2000 | Hooven et al. |
| 6,113,598 A | 9/2000 | Baker |
| 6,126,658 A | 10/2000 | Baker |
| 6,152,923 A | 11/2000 | Ryan |
| 6,174,309 B1 | 1/2001 | Wrublewski et al. |
| 6,183,467 B1 | 2/2001 | Shapeton et al. |
| 6,187,003 B1 | 2/2001 | Buysse et al. ............. 606/49 |
| 6,190,386 B1 | 2/2001 | Rydell |
| 6,206,877 B1 | 3/2001 | Kese et al. |
| 6,277,117 B1 | 8/2001 | Tetzlaff et al. ............. 606/48 |

OPEN VESSEL SEALING FORCEPS WITH DISPOSABLE ELECTRODES

CROSS REFERENCE TO RELATED APPLICATIONS

This application is a C-I-P of U.S. application Ser. No. 09/177,950 filed Oct. 23, 1998 by Randel A. Frazier et al., now abandoned and to U.S. application Ser. No. 09/178,027 filed Oct. 23, 1998 by Philip Mark Tetzlaff et al., U.S. Pat. No. 6,277,117 the entire contents of each of these applications are hereby incorporated by reference.

BACKGROUND

The present disclosure relates to electrosurgical forceps used for open surgical procedures and/or laparoscopic surgical procedures. More particularly, the present disclosure relates to a bipolar forceps having a disposable electrode assembly for sealing, cauterizing, coagulating/desiccating and/or cutting vessels and vascular tissue.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize, cut and/or seal tissue.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of end effectors and which are both electrically coupled to an electrosurgical generator. Each electrode is charged to a different electric potential. Since tissue is a conductor of electrical energy, when the effectors are utilized to clamp or grasp tissue therebetween, the electrical energy can be selectively transferred through the tissue.

The process of coagulating small vessels is fundamentally different than vessel sealing. For the purposes herein the term coagulation is defined as a process of desiccating tissue wherein the tissue cells are ruptured and dried. Vessel sealing is defined as the process of liquefying the collagen in the tissue so that it cross-links and reforms into a fused mass. Thus, coagulation of small vessels is sufficient to close them, however, larger vessels need to be sealed to assure permanent closure.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. No. 4,005,714 to Hiltebrandt, U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al., all relate to electrosurgical instruments for coagulating, cutting and/or sealing vessels or tissue.

These instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles.

Thus, a need exists to develop a bipolar forceps which can seal vessels and tissue consistently and effectively and which will not be damaged by continued use and cleaning.

SUMMARY

The present disclosure relates to a removable electrode assembly for use in combination with a mechanical forceps having opposed end effectors and a handle for controlling movement of the end effectors relative to one another. The electrode assembly includes a housing which is removably engageable with the mechanical forceps and a pair of electrodes which are attachable to a distal end of the housing. The electrodes are removably engageable with the end effectors of the mechanical forceps such that the electrodes reside in opposing relation relative to one another. Preferably, the electrode assembly can be employed with both open surgical procedures as well as laparoscopic surgical procedures.

Preferably, the distal end of the housing is bifurcated forming two prongs and each of the electrodes is attached to each of the prongs. In one embodiment, the prongs are movable relative to one another to facilitate engagement of the electrodes with the end effectors of the mechanical forceps.

Each electrode preferably includes an electrically conductive sealing surface and an insulating substrate. The, substrate includes at least one mechanical interface for engaging a complimentary mechanical interface disposed on the corresponding end effector of the mechanical forceps. In one embodiment the electrodes include at least one guide pin and the corresponding end effector includes a complimentary aperture for receiving the guide pin.

Preferably, the electrode assembly includes at least one stop member for controlling the distance between the opposing electrodes. In another embodiment of the present disclosure, the mechanical forceps includes at least one stop member for controlling the distance between the end effectors which, in turn, control the distance between the attached opposing electrodes.

Another embodiment of the present disclosure includes a cover plate which is removably engageable with the housing member and the mechanical forceps are disposed between the housing and the cover plate when the bipolar forceps is assembled.

Another embodiment includes a removable electrode assembly which includes a housing having at least one portion which is removably engageable with at least one portion of the forceps and a pair of electrodes attachable to a distal end of the housing. Preferably, the electrodes are removably engageable with the end effectors of the forceps such that the electrodes reside in opposing relation relative to one another. Preferably, the electrodes are electrically isolated from the handle.

Another embodiment includes a bipolar forceps which includes a mechanical forceps having opposing end effectors and a handle for effecting movement of the end effectors relative to one another and an electrode assembly which removably engages the mechanical forceps. A pair of opposing electrodes are attached to a distal end of the electrode assembly and are removably engageable with one of the end effectors such that the electrodes reside in opposing relation relative to one another. Preferably, at least one stop member controls the distance between the opposing electrodes.

Still yet another embodiment includes a bipolar electrosurgical instrument which includes a pair of first and second members each having an end effector attached to a distal end thereof and a handle attached to a proximal end thereof for effecting movement of the end effectors relative to one another. An electrode assembly is removably engageable with one of the first or second members and has a pair of electrodes which are removably engageable with the end effectors.

Another embodiment includes a bipolar electrosurgical instrument having a pair of first and second members each having an end effector attached to a distal end thereof and a handle movable from a first position wherein the first and second members are disposed in spaced relation relative to one another to a second position wherein the members are closer relative to one another. A first electrode removably mounts to the first end effector and a second electrode removably mounts to the second end effector.

Yet another embodiment includes a bipolar electrosurgical instrument having at least one stop member for maintaining a gap distance between the opposing electrodes, the gap distance being in the range of about 0.001 inches to about 0.006 inches.

DETAILED DESCRIPTION OF THE PREFERRED EMBODIMENTS

Figure 1:
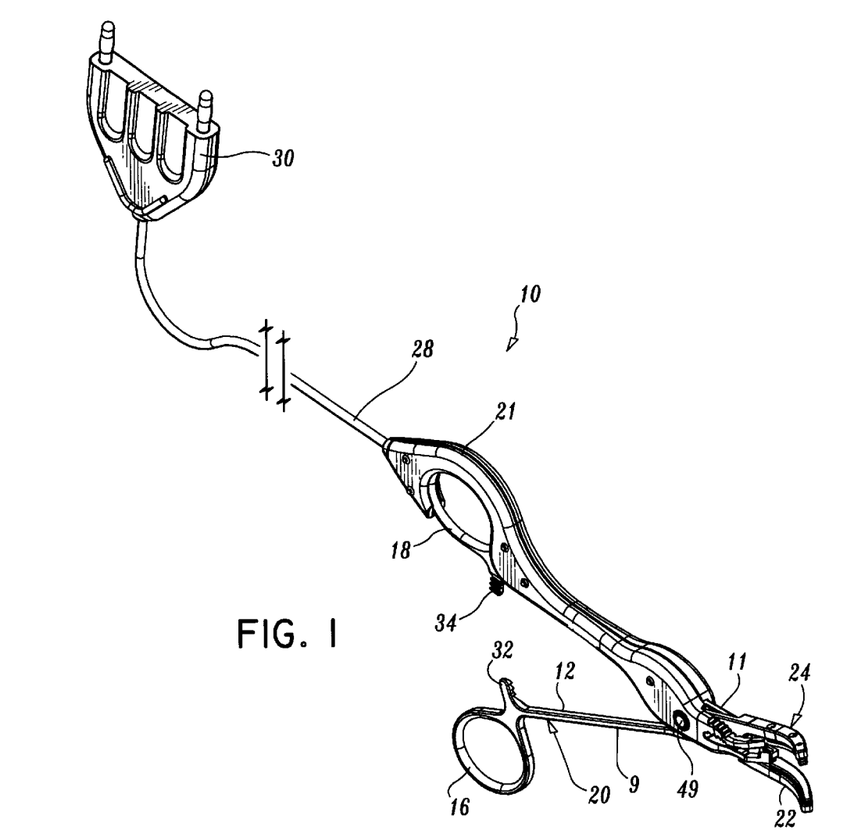
FIG. 1 is a perspective view of a bipolar forceps according to the present disclosure.
Figure 2:
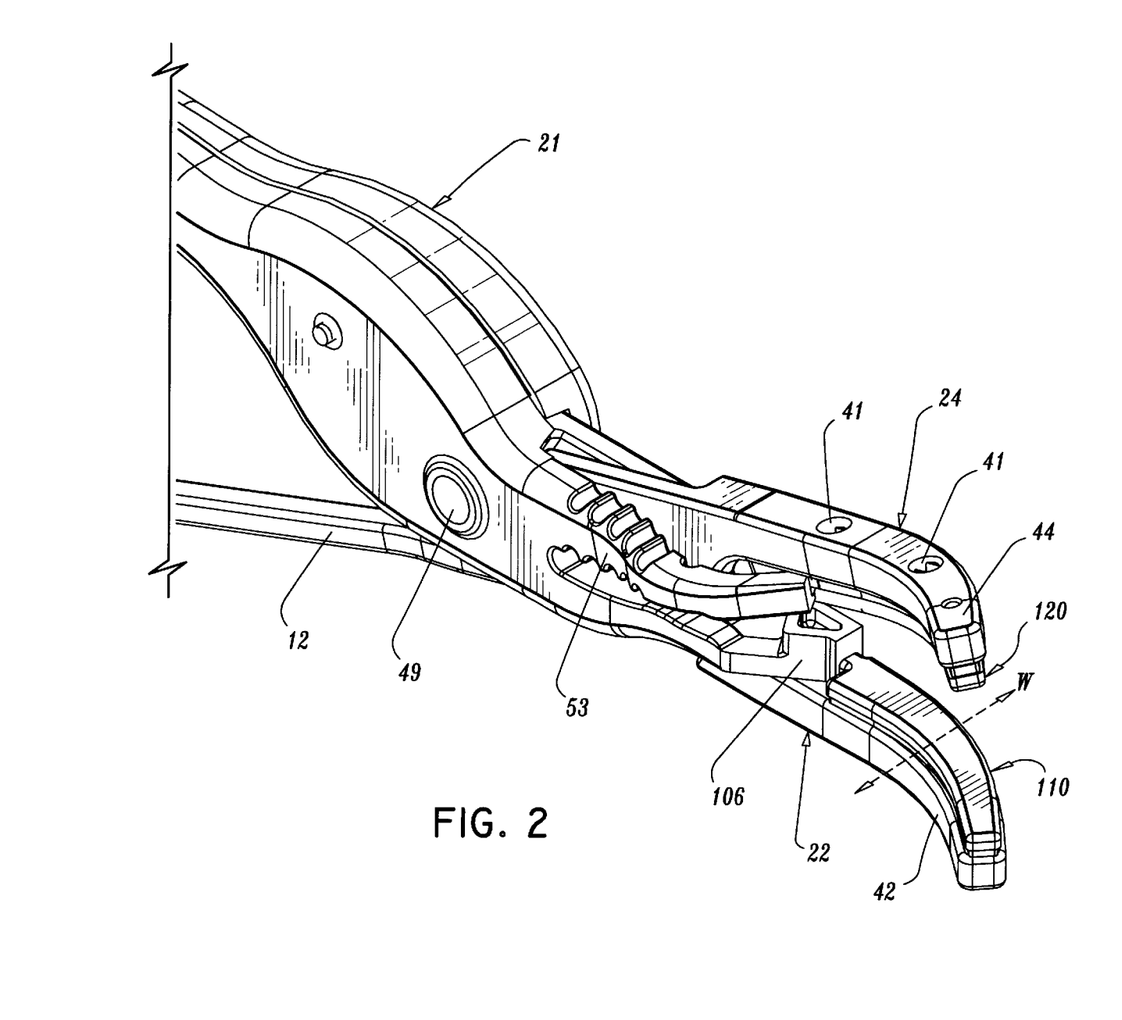
FIG. 2 is an enlarged, perspective view of a distal end of the bipolar forceps shown in FIG. 1.
Figure 3:
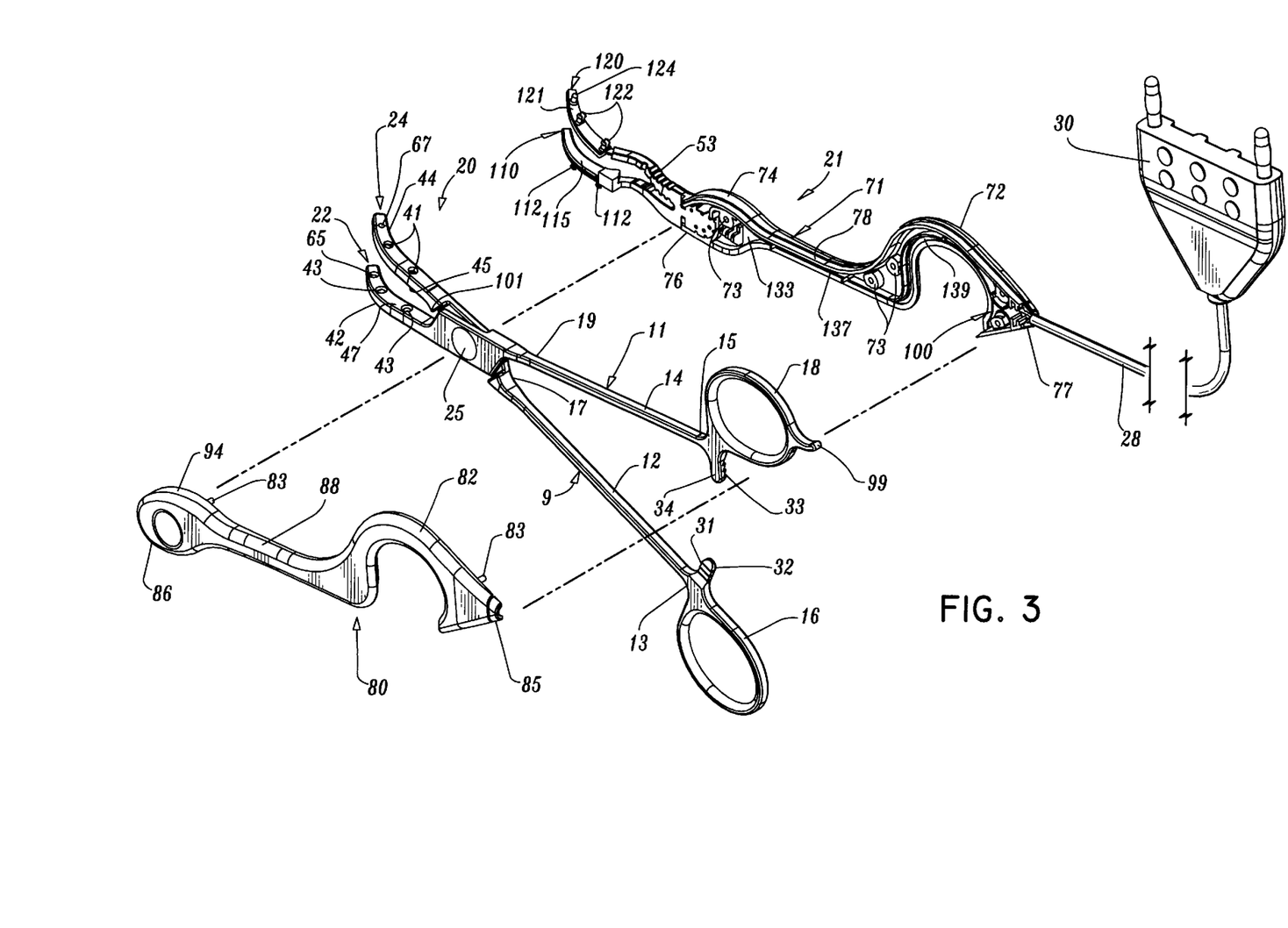
FIG. 3 is a perspective view with parts separated of the forceps shown in FIG. 1.

Referring now to FIGS. 1–3, a bipolar forceps 10 for use with open and/or laparoscopic surgical procedures includes a mechanical forceps 20 and an electrode assembly 21. In the drawings and in the description which follows, the term "proximal", as is traditional, will refer to the end of the forceps 10 which is closer to the user, while the term "distal" will refer to the end which is further from the user.

Mechanical forceps 20 includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto to allow a user to effect movement of at least one of the shaft portions 12 and 14 relative to one another; Extending from the distal end 17 and 19 of each shaft portion 12 and 14 are end effectors 22 and 24, respectively. The end effectors 22 and 24 are movable relative to one another in response to movement of handle members 16 and 18.

Figure 8:
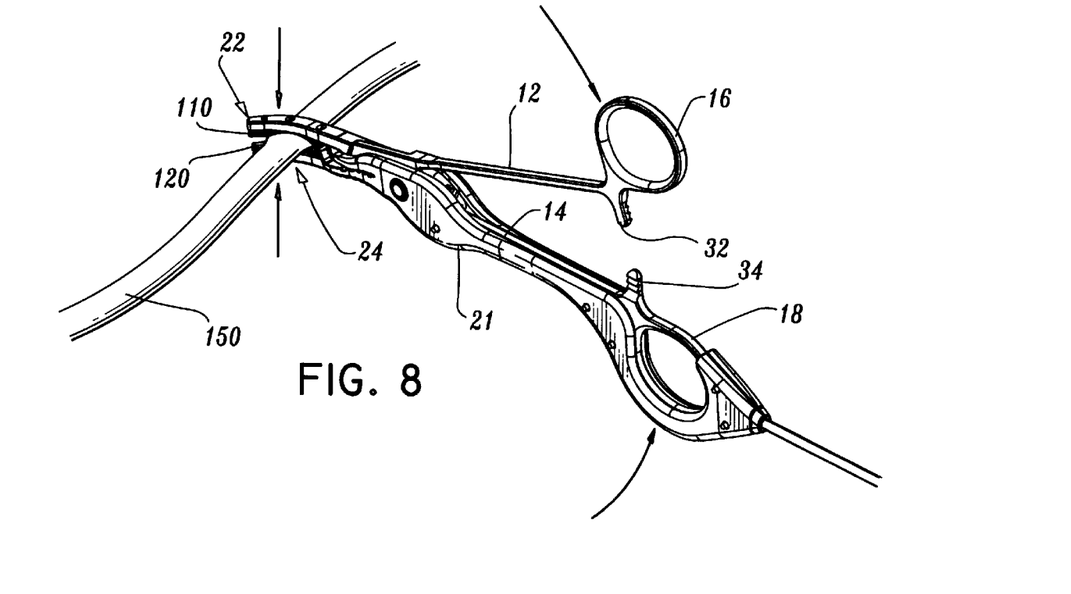
FIG. 8 is a perspective view of the forceps of the present disclosure showing the operative motion of the forceps to effect sealing of a tubular vessel.

Preferably, shaft portions 12 and 14 are affixed to one another at a point proximate the end effectors 22 and 24 about a pivot 25 such that movement of the handles 16 and 18 impart movement of the end effectors 22 and 24 from an open position wherein the end effectors 22 and 24 are disposed in spaced relation relative to one another to a clamping or closed position wherein the end effectors 22 and 24 cooperate to grasp a tubular vessel 150 therebetween (see FIG. 8). It is envisioned that pivot 25 has a large surface area to resist twisting and movement of forceps 10 during operation. Clearly, the forceps 10 can be designed such that movement of one or both of the handles 16 and 18 will only cause one of the end effectors, e.g., 22, to move with respect to the other end effector, e.g., 24.

As best seen in FIG. 3, end effector 24 includes an upper or first jaw member 44 which has an inner facing surface 45 and a plurality of mechanical interfaces disposed thereon which are dimensioned to releasable engage a portion of a disposable electrode assembly 21 which will be described in greater detail below. Preferably, the mechanical interfaces include sockets 41 which are disposed at least partially through inner facing surface 45 of jaw member 44 and which are dimensioned to receive a complimentary detent attached to upper electrode 120 of the disposable electrode assembly 21. While the term socket is used herein, it is contemplated that either a male or female mechanical interface may be used on jaw member 44 with a mating mechanical interface disposed on the disposable electrode assembly 21.

In some cases, it may be preferable to manufacture mechanical interfaces 41 along another side of jaw member 44 to engage a complimentary mechanical interface of the disposable electrode assembly 21 in a different manner, e.g., from the side. Jaw member 44 also includes an aperture 67 disposed at least partially through inner face 45 of end effector 24 which is dimensioned to receive a complimentary guide pin 124 disposed on electrode 120 of the disposable electrode assembly 21.

End effector 22 includes a second or lower jaw member 42 which has an inner facing surface 47 which opposes inner facing surface 45. Preferably, jaw members 45 and 47 are dimensioned generally symmetrically, however, in some cases it may be preferable to manufacture the two jaw members 42 and 44 asymmetrically depending upon a particular purpose. In much the same fashion as described above with respect to jaw member 44, jaw member 42 also includes a plurality of mechanical interfaces or sockets 43 disposed thereon which are dimensioned to releasable engage a complimentary portion disposed on an electrode 110 of the disposable electrode assembly 21 as described below. Likewise, jaw member 42 also includes an aperture 65 disposed at least partially through inner face 47 which is dimensioned to receive a complimentary guide pin 126 (see FIG. 4) disposed on electrode 110 of the disposable electrode assembly 21.

Preferably, shaft members 12 and 14 of the mechanical forceps 20 are designed to transmit a particular desired force to the opposing inner facing surfaces 47 and 45 of the of the jaw members 22 and 24, respectively, when clamped. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34. Preferably, each ratchet, e.g., 32, extends from the proximal end 13 of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. Preferably, each ratchet position holds a specific, i.e., constant, strain energy in the shaft members 12 and 14 which, in turn, transmit a specific force to the end effectors 22 and 24 and, thus, the electrodes 120 and 110. A design without a ratchet system or similar system would require the user to hold the jaw members 42 and 44 together by applying constant force to the handles 16 and 18 which may yield inconsistent results.

In some cases it may be preferable to include other mechanisms to control and/or limit the movement of the jaw members 42 and 44 relative to one another. For example, a ratchet and pawl system could be utilized to segment the movement of the two handles into discrete units which will, in turn, impart discrete movement to the jaw members 42 and 44 relative to one another.

Preferably, at least one of the shaft members, e.g., 14, includes a tang 99 which facilitates manipulation of the forceps 20 during surgical conditions as well as facilitates attachment of electrode assembly 21 on mechanical forceps 20 as will be described in greater detail below.

Figures 5, 6, 7:
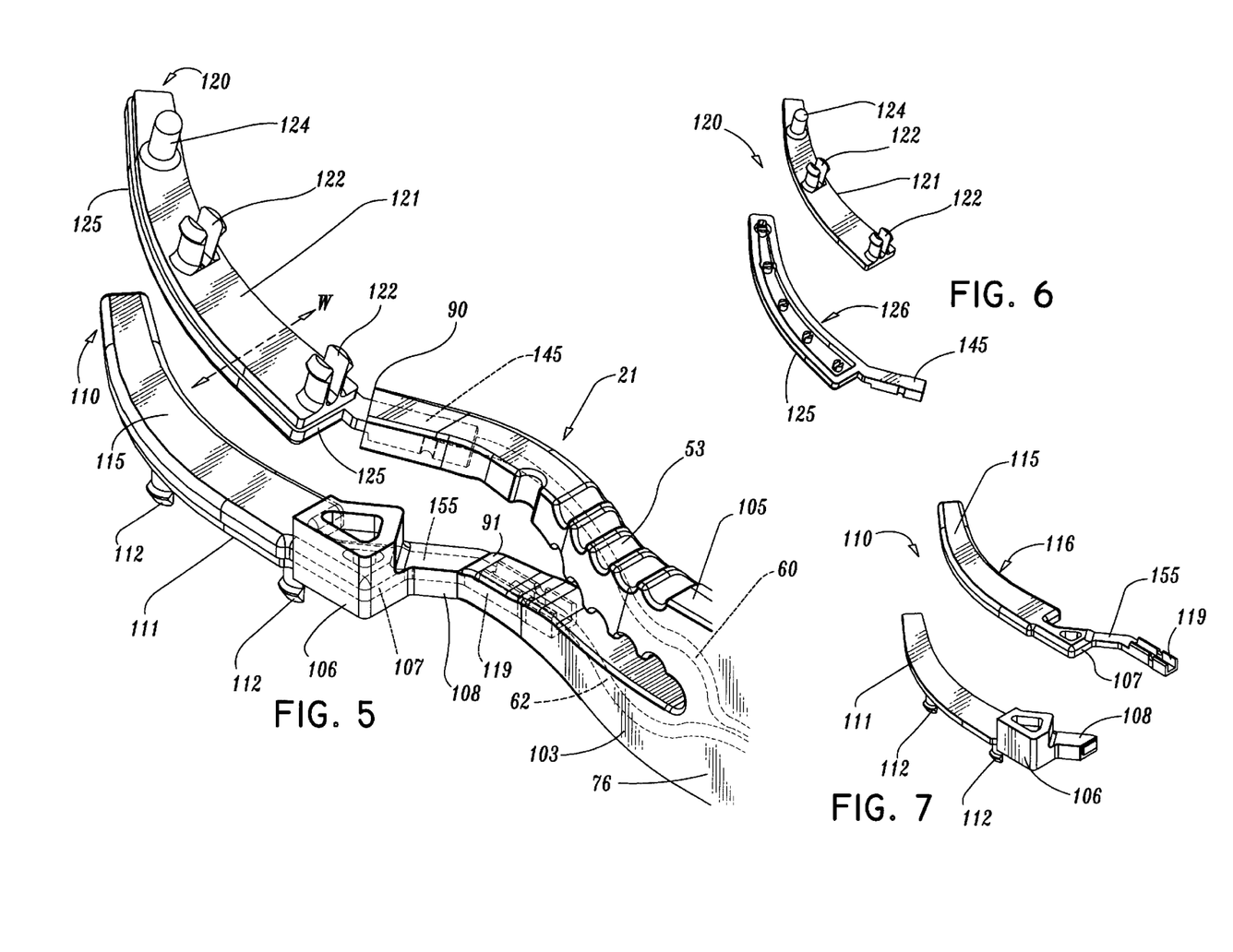
FIG. 5 is an enlarged, perspective view of a distal end of the disposable electrode assembly of FIG. 4.
FIG. 6 is a perspective view with parts separated of an upper electrode of the disposable electrode assembly of FIG. 5.
FIG. 7 is a perspective view with parts separated of a lower electrode of the disposable electrode assembly of FIG. 5.

As best seen in FIGS. 2, 3 and 5, disposable electrode assembly 21 is designed to work in combination with mechanical forceps 20. Preferably, electrode assembly 21 includes housing 71 which has a proximal end 77, a distal end 76 and an elongated shaft plate 78 disposed therebetween. A handle plate 72 is disposed near the proximal end 77 of housing 71 and is sufficiently dimensioned to releasably engage and/or encompass handle 18 of mechanical forceps 20. Likewise, shaft plate 78 is dimensioned to encompass and/or releasably engage shaft 14 and pivot plate 74 disposed near the distal end 76 of housing 71 is dimensioned to encompass pivot 25 and at least a portion of distal end 19 of mechanical forceps 20. It is contemplated that the electrode assembly 21 can be manufactured to engage either the first or second members 9 and 11 of the mechanical forceps 20 and their respective component parts 12, 16 or 14, 18, respectively.

In the embodiment shown in FIG. 2, handle 18, shaft 14, pivot 25 and a portion of distal end 19 are all dimensioned to fit into corresponding channels located in housing 71. For example, a channel 139 is dimensioned to receive handle 18, a channel 137 is dimensioned to receive shaft 14 and a channel 133 is dimensioned to receive pivot 25 and a portion of distal end 19.

Electrode assembly 21 also includes a cover plate 80 which is also designed to encompass and/or engage mechanical forceps 20 in a similar manner as described with respect to the housing 71. More particularly, cover plate 80 includes a proximal end 85, a distal end 86 and an elongated shaft plate 88 disposed therebetween. A handle plate 82 is disposed near the proximal end 85 and is preferably dimensioned to releasable engage and/or encompass handle 18 of mechanical forceps 20. Likewise, shaft plate 88 is dimensioned to encompass and/or releasable engage shaft 14 and a pivot plate 94 disposed near distal end 86 is designed to encompass pivot 25 and distal end 19 of mechanical forceps 20. Preferably, handle 18, shaft 14, pivot 25 and distal end 19 are all dimensioned to fit into corresponding channels (not shown) located in cover plate 80 in a similar manner as described above with respect to the housing 71.

Figure 4:
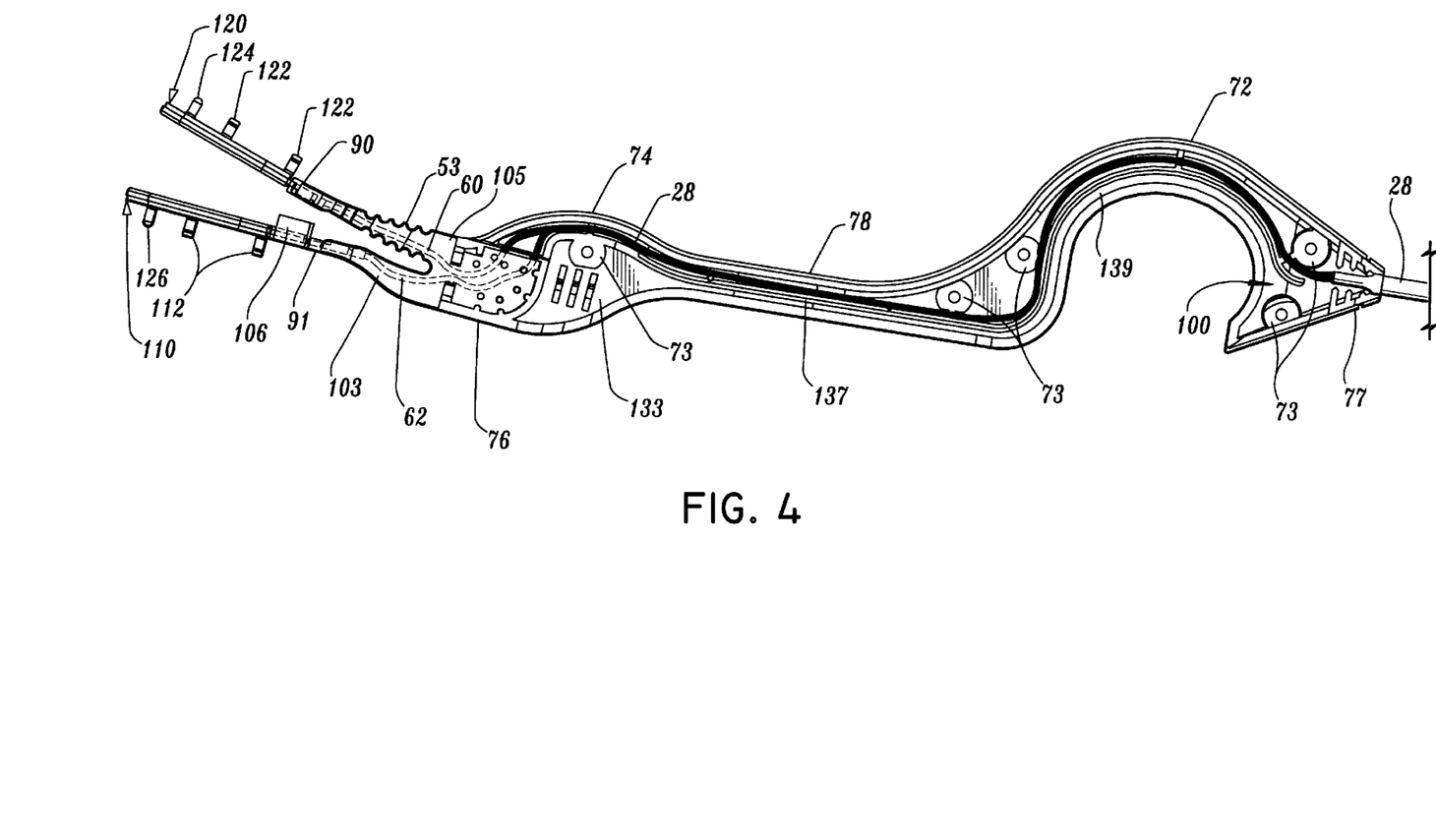
FIG. 4 is an enlarged, side view of a disposable electrode assembly of FIG. 1 shown without a cover plate.

As best seen with respect to FIGS. 3 and 4, housing 71 and cover plate 80 are designed to engage one another over first member 11 of mechanical forceps 20 such that first member 11 and its respective component parts, e.g., handle 18, shaft 14, distal end 19 and pivot 25, are disposed therebetween. Preferably, housing 71 and cover plate 80 include a plurality of mechanical interfaces disposed at various positions along the interior of housing 71 and cover plate 80 to effect mechanical engagement with one another. More particularly, a plurality of sockets 73 are disposed proximate handle plate 72, shaft plate 78 and pivot plate 74 of housing 71 and are dimensioned to releasably engage a corresponding plurality of detents 83 extending from cover plate 80. It is envisioned that either male or female mechanical interfaces or a combination of mechanical interfaces may be disposed within housing 71 with mating mechanical interfaces disposed on or within cover plate 80.

As best seen with respect to FIGS. 5–7, the distal end 76 of electrode assembly 21 is bifurcated such that two prong-like members 103 and 105 extend outwardly therefrom to support an electrode 110 and 120, respectively. More particularly, electrode 120 is affixed at an end 90 of prong 105 and electrode 110 is affixed at an end 91 of prong 103. It is envisioned that the electrodes 110 and 120 can be affixed to the ends 91 and 90 in any known manner such as, e.g., frictional or snap-fit engagement.

A pair of wires 60 and 62 are connected to the electrodes 120 and 110, respectively, as best seen in FIGS. 4 and 5. Preferably, wires 60 and 62 are bundled together and form a wire bundle 28 which runs from a terminal connector 30 (see FIG. 3), to the proximal end 77 of housing 71, along the interior of housing 71, to distal end 76. Wire bundle 28 is separated into wires 60 and 62 proximate distal end 76 and the wires 60 and 62 are connected to each electrode 120 and 110, respectively. In some cases it may be preferable to capture the wires 60 and 62 or the wire bundle 28 at various pinch points along the inner cavity of the electrode assembly 21 and enclosing the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases it may be preferable to extend wires 60 and 62 to an electrosurgical generator (not shown). Alternatively, wires 60 and 62 can remain separated and extend along the first and second members 9 and 11.

As best seen in FIG. 6, electrode 120 includes an electrically conductive seal surface 126 and an electrically insulative substrate 121 which are attached to one another by snap-fit engagement or some other method of assembly, e.g., substrate 121 is overmolded to capture the electrically conductive seal surface 126. Preferably, substrate 121 is made from an injection molded plastic material and is shaped to mechanically engage a corresponding socket 41 located in jaw member 44 of end effector 24. The substrate 121 not only insulates the electric current but it also aligns electrode 120 both of which contribute to the seal quality and consistency. For example, by overmolding the conductive surface 126 to the substrate 121, the alignment and thickness of the electrode 120 can be controlled.

Preferably, substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44.

Conductive seal surface 126 includes an wire crimp 145 designed to engage the distal end 90 of prong 105 of electrode assembly 21 and electrically engage a corresponding wire connector affixed to wire 60 located within electrode assembly. Seal surface 126 also includes an opposing face 125 which is designed to conduct an electrosurgical current to a tubular vessel or tissue 150 when it is held thereagainst.

Electrode 110 includes similar elements for insulating and conducting electrosurgical current to tissue 150. More particularly, electrode 110 includes an electrically conductive seal surface 116 and an electrically insulative substrate 111 which are attached to one another by snap-fit engagement or some other method of assembly. Substrate 111 includes a plurality of bifurcated detents 112 and an alignment pin 126 (see FIG. 4) which are dimensioned to engage a corresponding plurality of sockets 43 and aperture 65 located in jaw member 42. Conductive seal surface 116 includes an extension 155 having a wire crimp 119 which engages the distal end 91 of prong 103 and electrically engages a corresponding wire connector affixed to wire 62 located in housing 71. Seal surface 116 also includes an opposing face 115 which conducts an electrosurgical current to a tubular vessel or tissue 150 when it is held thereagainst. Alternatively, electrodes 110 and/or 120 can be formed as one piece and include similar components for insulating and conducting electrical energy.

As best seen in FIG. 7, substrate 111 also includes an extension 108 and a stop member 106 which is designed to engage corresponding extension 155 and an interface 107 located on conductive seal 116. To assemble electrode 110, stop member 106 and extension 108 are overmolded onto interface 107 and extension 155 of conductive seal 116. After assembly, wire crimp 119 is then inserted into end 91 of prong member 103 and connected to wire 62.

It is known that as the tissue is compressed and electrosurgical energy is applied to the tissue, the impedance of the tissue decreases as the moisture level decreases. As a result, two mechanical factors play an important role in determining seal thickness and effectiveness, i.e., the pressure applied between opposing faces 47 and 45 and the gap distance between the opposing electrodes 110 and 120 (see FIG. 5). Jaw members 42 and 44 are configured to provide for the opposing electrodes 110 and 120 to be in a desired gap range (e.g., 0.001 and 0.006 inches) at the end of the tissue sealing process (See FIG. 8). The material conditions and components relating to the assembly of the electrode assembly 21 and the mechanical forceps 20 are configured to fall within specific manufacturing tolerances to assure that the gap between electrodes will not vary outside the desired range.

It is also known that tissue thickness is very difficult to control by force alone, i.e., too much force and the two poles would touch and the little energy would travel through the tissue resulting in a bad seal or too little force and the seal would be too thick. Applying the correct force is important for other reasons: to oppose the vessel lumens; reduce the tissue impedance to a low enough value that allows enough current through the tissue; and to overcome the forces of expansion during tissue heating in addition to contributing towards creating the required end tissue thickness which is an indication of a good seal.

It is also known that the size of the gap effects the tissue seal. For example, if a gap is too great, i.e., the jaws do not compress the tissue enough, the tissue does not properly liquefy the collagen for effective sealing. If, on the other hand, the gap is too small, i.e., the jaws compress the tissue too much, the electrosurgical energy effectively severs the tissue which is also undesirous. It has been found that in order to effectively seal tissue and overcome the shortcomings described above, the gap distance (range) 151 (See FIG. 8) between the opposing electrodes 110 and 120 is preferably between about 0.001 inches to about 0.006 inches and more preferably, between about 0.002 inches to about 0.005 inches.

In order to assure that the desired gap range is achieved after assembly and that the correct force is applied to seal the tissue, substrate 111 includes at least one stop member, 106, which is designed to restrict and/or regulate movement of the two electrodes 110 and 120 relative to one another. Preferably, forceps 20 also includes at least one stop member, e.g., 101 (see FIG. 3), for restricting and/or regulating the distance between end effectors 22 and 24 and/or the closure force applied between opposing inner facing surfaces 47 and 45 of end effectors 22 and 24 which will, in turn, regulate the distance between electrodes 110 and 120. Since stop 106 is part of the disposable electrode assembly 21, this stop has the added benefit of being dependent on the material of the disposable electrode assembly 21. Preferably, a "step" stop is utilized due to its ease of manufacture and simplicity.

It is contemplated that the stop member can be positioned at various points along the disposable electrode assembly to achieve the aforedescribed desired gap range and/or the stop member can be positioned on other parts of the instrument, e.g., handles 16, 18, jaws 42, 44, and/or shafts 12, 14.

Preferably, the seal surfaces 115 and 125 are relatively flat to avoid current concentrations at sharp edges and to avoid arcing between high points. In addition and due to the reaction force of the tissue 150 when engaged, jaw members 42 and 44 are preferably manufactured to resist bending. For example and as best seen in FIG. 3, the jaw members 42 and 44 and the corresponding electrodes 110 and 120 are preferably tapered along width "W" which is advantageous for two reasons: 1) the taper will apply constant pressure for a constant tissue thickness at parallel; 2) the thicker proximal portion of the electrode, e.g., 110, will resist bending due to the reaction force of the tissue 150. The tapered shape of the electrode, e.g., 110, is determined by calculating the mechanical advantage variation from the distal to proximal end of the electrode 110 and adjusting the width of the electrode 110 accordingly.

Preferably, at least one of the prong members, e.g., 105, is resilient or includes a flex relief portion 53 which permits movement of the two prong members 105 and 103 and, thus, the two electrodes 120 and 110, relative to one another. As seen best in FIG. 3, the electrode assembly 21 is removably attached to the mechanical forceps 20 by initially moving prong 105 towards prong 103 by bending prong 105 at flex relief portion 53. The electrodes 110 and 120 are then slid between opposing jaw members 42 and 44 in their open position such that detents 112 and 122 and guide pins 126 and 124, respectively, are each disposed in alignment with each corresponding socket 43 and 41 or aperture 65 and 67, respectively. Housing 71 is also positioned accordingly such that shaft 14, handle 18 and pivot 25 are all positioned proximate their corresponding channels 137, 139 and 133 located within housing 71.

When flex relief portion 53 is released, each electrode 110 and 120 is engaged with jaw member 42 and 44, respectively, i.e., detents 112, 122 engage sockets 43, 41, and housing 71 is engaged with mechanical forceps 20. The cover plate 80 is then attached to housing 71 in the manner described above. The bipolar forceps 10 is now ready for operation.

In one embodiment, the electrode assembly 21 is attached to the mechanical forceps 20 in a different manner: For example and as best illustrated in FIG. 3, the electrode assembly 21 can be engaged, with the mechanical forceps 20 in the following four-step manner: 1) electrode assembly 21 and cover plate 80 are pivoted backward such that tang 99 engages a slot 100 in electrode assembly 21; 2) electrode assembly 21 and cover plate 80 are then pivoted forward to engage shaft 14 of mechanical forceps 20 therebetween; 3) detents 112 of electrode 110 are then engaged with sockets 43 of jaw member 22; and 4) detents 122 of electrode 120 are engaged with sockets 41 of jaw member 24.

Figure 9:
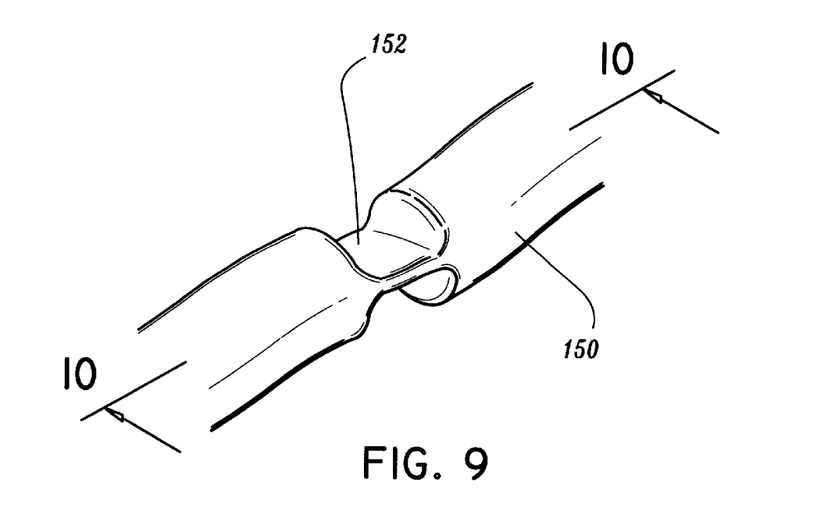
FIG. 9 is an enlarged, partial perspective view of a sealing site of a tubular vessel.
Figure 10:
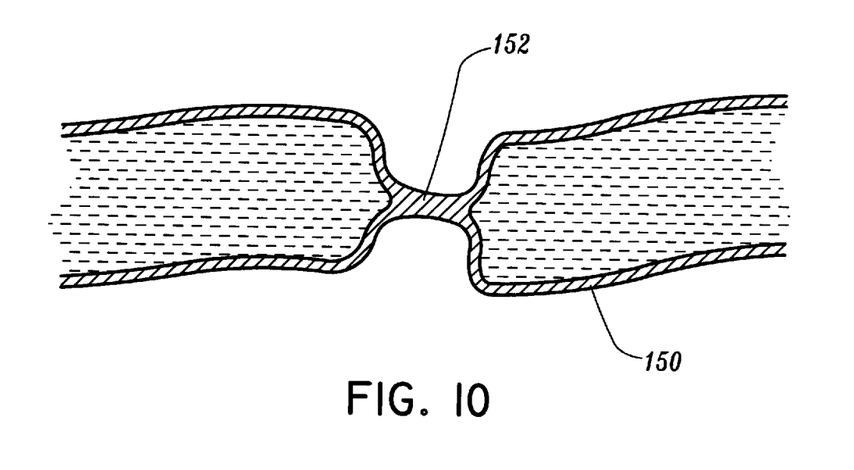
FIG. 10 is a longitudinal cross-section of the sealing site taken along line 10—10 of FIG. 9.
Figure 11:
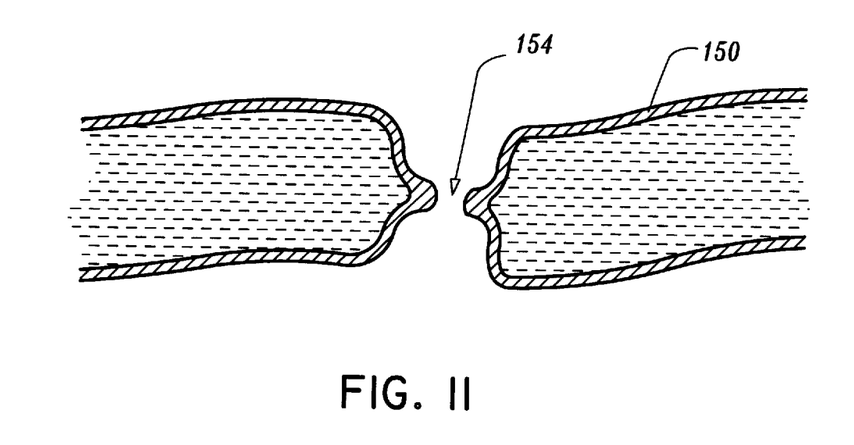
FIG. 11 is a longitudinal cross-section of the sealing site of FIG. 9 after separation of the tubular vessel.

FIG. 8 shows the. bipolar forceps 10 during use wherein the handle members 16 and 18 are moved closer to one another to apply clamping force to the tubular tissue 150 to effect a seal 152 as shown in FIGS. 9 and 10. Once sealed, the tubular vessel 150 can be cut along seal 152 to separate the tissue 150 and form gap 154 therebetween as shown in FIG. 11.

After the bipolar forceps 10 is used or if the electrode assembly 21 is damaged, the electrode assembly 21 can be easily removed and/or replaced by reversing the above attachment procedure and a new electrode assembly 21 can be engaged with the mechanical forceps 20 in the same manner. For example, the electrode assembly 21 can be disengaged from the mechanical forceps 20 in the following four-step manner: 1) the detents 122 of electrode 120 are disengaged from the sockets 41 of jaw member 24; 2) the detents 112 of electrode 110 are disengaged from the sockets 43 of jaw member 22; 3) the electrode assembly 21 and cover plate 80 are disengaged from shaft 14 of mechanical forceps 20; and 4) the electrode assembly 21 and cover plate 80 are pivoted such that tang 99 disengages from slot 100 in electrode assembly 21.

It is envisioned that by making the electrode assembly 21 disposable, the electrode assembly 21 is less likely to become damaged since it is only intended for a single use and, therefore, does not require cleaning or sterilization. As a result, the functionality and consistency of the vital sealing components, e.g., the conductive surface 126, 116 and insulating surface 121, 111 will assure a uniform and quality seal.

Figure 12:
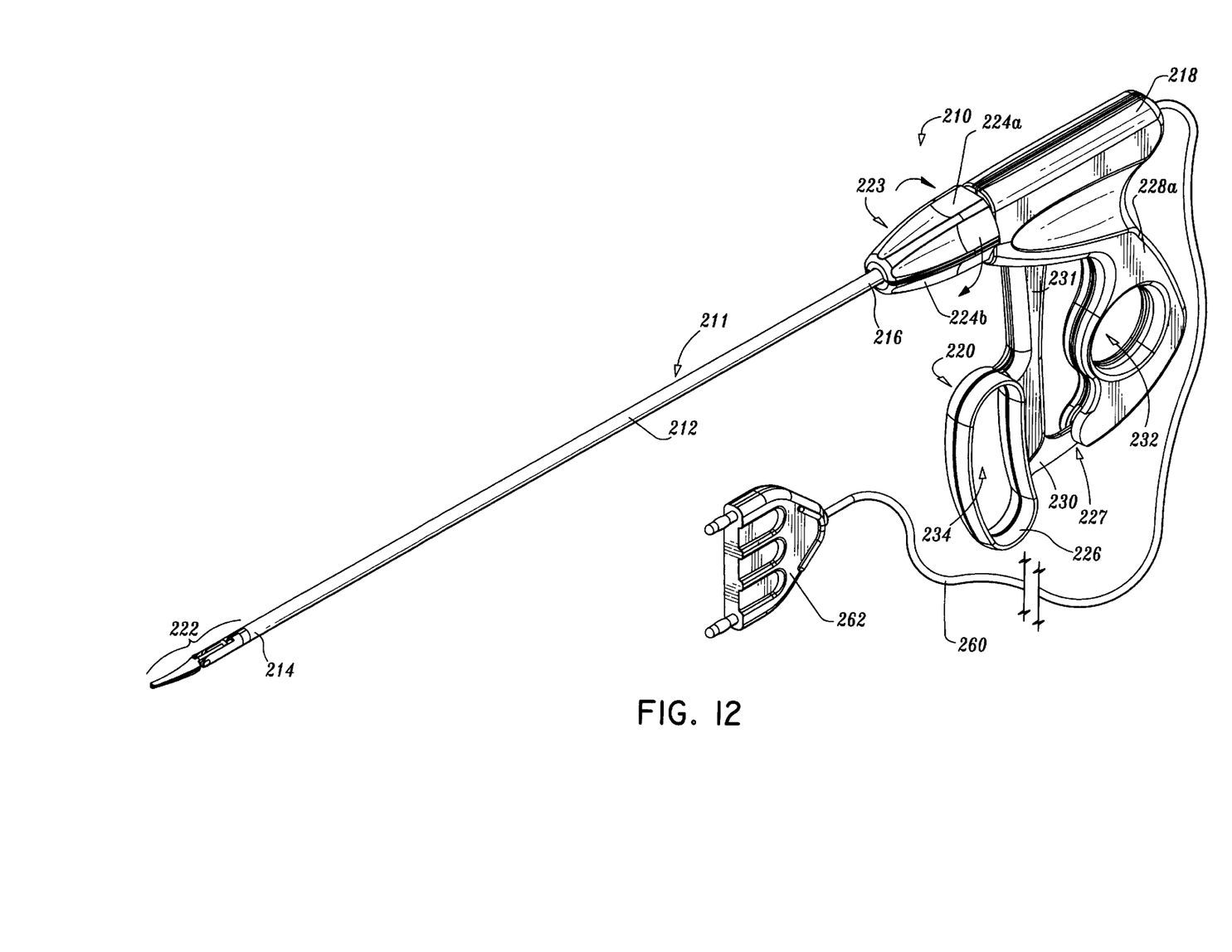
FIG. 12 is a perspective view of another embodiment of the present disclosure.
Figure 13:
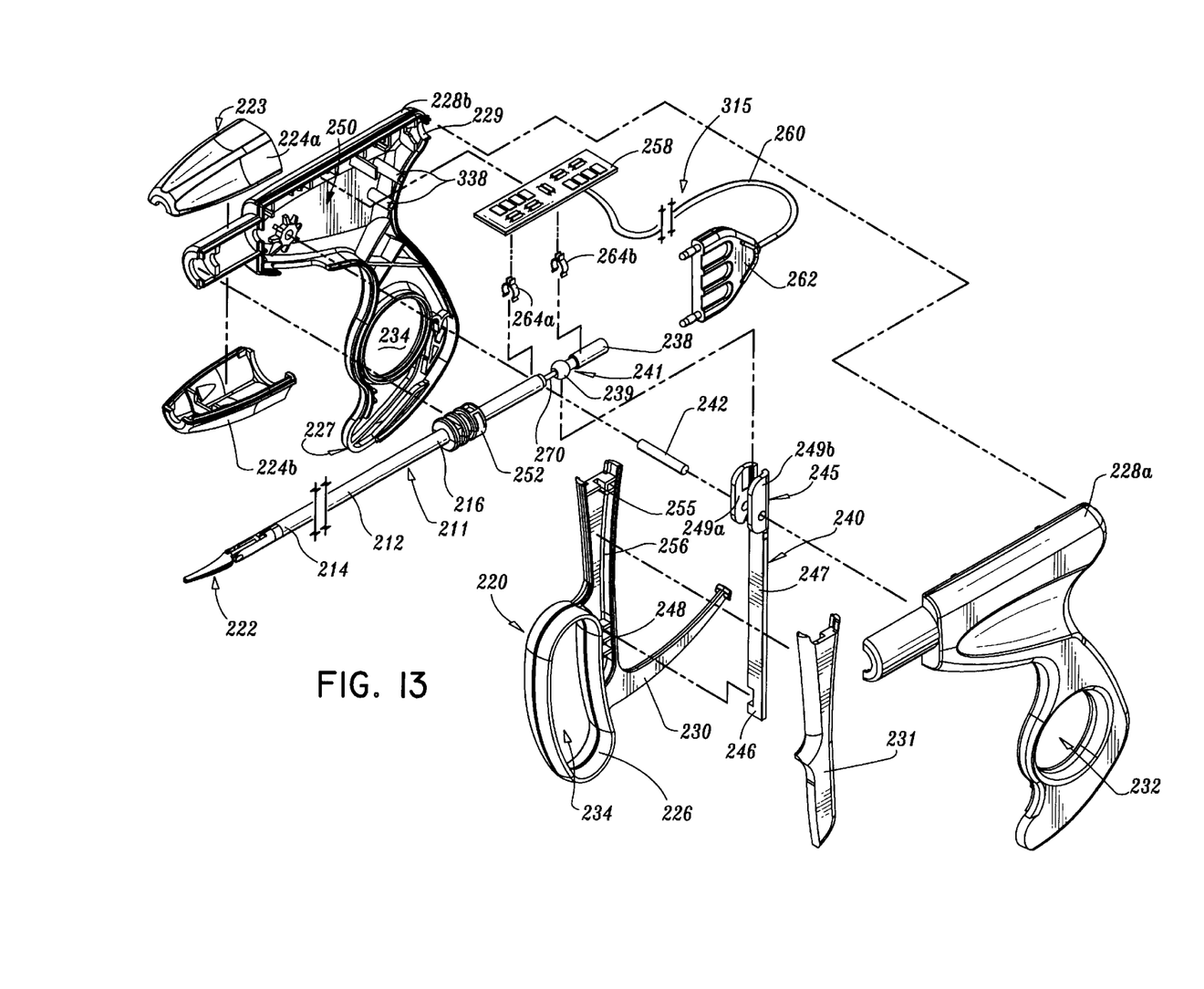
FIG. 13 is an exploded view of the embodiment of FIG. 12.
Figure 14:
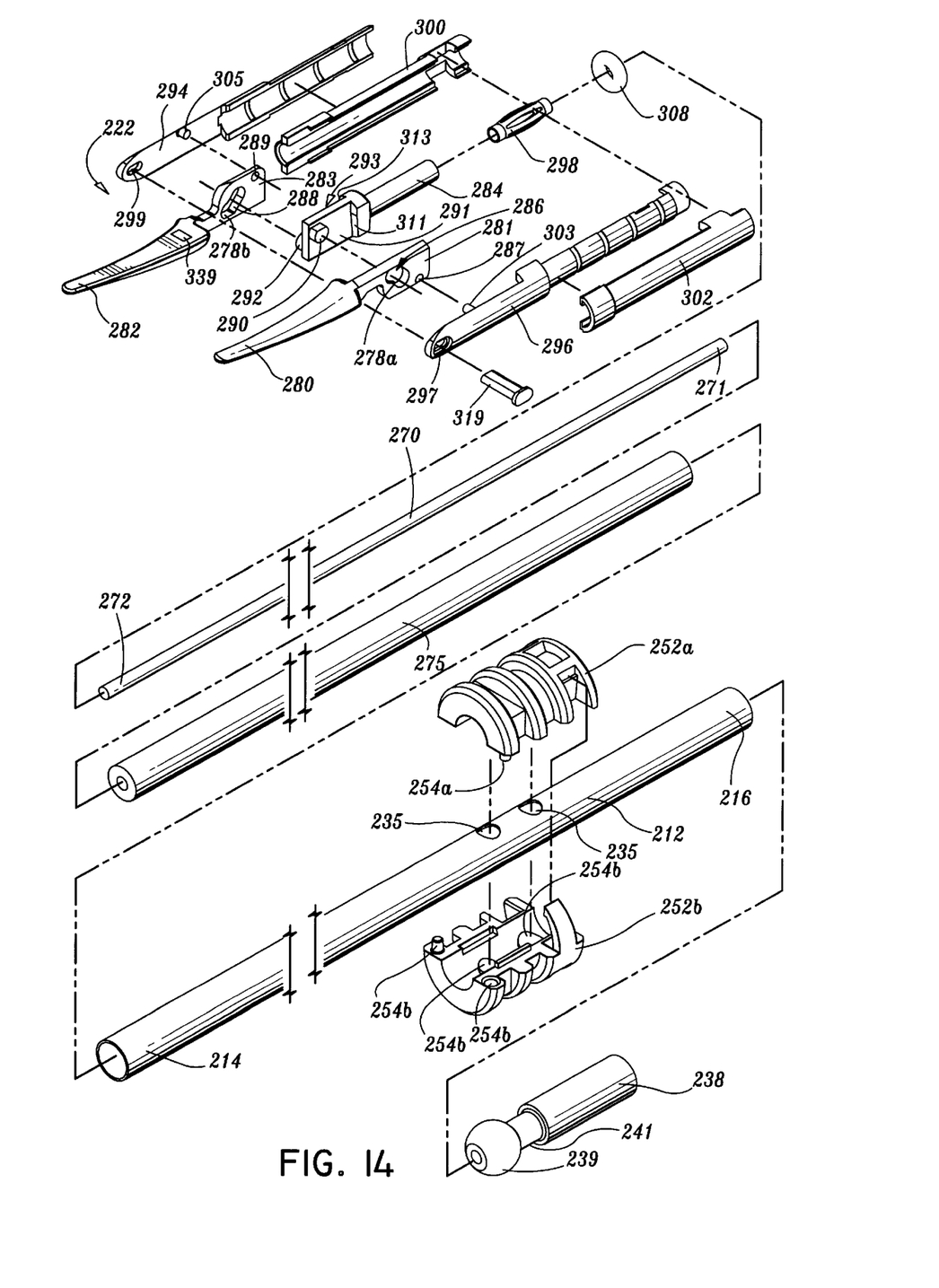
FIG. 14 is an enlarged exploded view of a working end of the embodiment of FIGS. 12 and 13.

FIGS. 12–14 show another embodiment of the present disclosure for use with endoscopic surgical procedures and includes a bipolar forceps 210 having a drive rod assembly 211 coupled to a handle assembly 218. The drive rod assembly 211 includes an elongated hollow shaft portion 212 having a proximal end 216 and a distal end 214. An end effector assembly 222 is attached to the distal end 214 of shaft 212 and includes a pair of opposing jaw members 280 and 282. Preferably, handle assembly 218 is attached to the proximal end 216 of shaft 212 and includes an activator 220 for imparting movement of the jaw members 280 and 282 from an open position wherein the jaw members 280 and 282 are disposed in spaced relation relative to one another, to a clamping or closed position wherein the jaw members 280 and 282 cooperate to grasp tissue 150 therebetween.

As best seen in FIG. 13, activator 220 includes a movable handle 226 having an aperture 234 defined therein for receiving at least one of the operator's fingers and a fixed handle 228 having an aperture 232 defined therein for receiving an operator's thumb. Movable handle 226 is selectively moveable from a first position relative to fixed handle 228 to a second position in closer proximity to the fixed handle 228 to close jaw members 280 and 282. Preferably, fixed handle 228 includes a channel 227 which extends proximally for receiving a ratchet 230 which is coupled to movable handle 226. This structure allows for progressive closure of end effector assembly 222 as well as locking engagement of opposing jaw members 280 and 282. In some cases it may be preferable to include other mechanisms to control and/or limit the movement of handle 226 relative to handle 228 such as, e.g., hydraulic, semi-hydraulic and/or gearing systems.

Fixed handle 228 includes a rotating assembly 223 for controlling the rotational movement of end effector assembly 222 about a longitudinal axis "A" of the elongated shaft 212. Preferably, rotating assembly 223 includes upper and lower knob portions 224a and 224b, respectively, which releasably engage one another about a gear 252 which is attached to shaft 212. A pair of handle sections 228a and 2228b engage one another by way of a plurality of mechanical interfaces to form fixed handle 228. As best seen in FIG. 13, each handle section 228a and 228b is generally hollow such that a cavity 250 is formed therein for housing various internal components which make up the forceps 210. For example, cavity 250 houses a PC board 258 which controls the electrosurgical energy being transmitted from an electrosurgical generator (not shown) to each jaw member 280 and 282. More particularly, electrosurgical energy is generated from an electrosurgical generator and transmitted to the PC board by cable 260 which attached through a wire port 229 disposed in the proximal end of handle assembly 218. The PC board 258 converts the electrosurgical energy from the generator into two different electrical potentials which are transmitted to each jaw member 280 and 282 by a separate terminal clip 264b and 264a, respectively, which will be explained in more detail below with respect to FIG. 14.

Referring to FIG. 14, rod assembly 211 includes a drive rod 270 which has a proximal end 271 and a distal end 272. A piston 238 is attached to the proximal end 271 of drive rod 270 and includes a generally rounded head portion 239 and a notch 241 located between the head portion 239 and the proximal end of piston 238. Preferably, clevis flanges 249a and 249b of arm 240 are dimensioned to receive head 239 therebetween when arm 240 is assembled between handle sections 228a and 228b (see FIG. 6). Movement of the handle 226 towards fixed handle 228 imparts pivotal movement of the upper end 245 of arm 240 at a pivot point 255 which, in turn, imparts movement of the piston 238 from a first position wherein the piston 238 is disposed further from end effector assembly 222 to a second position wherein piston 238 is in closer proximity to end effector assembly 222. As explained in greater detail below, movement of the piston 238 between first and second positions imparts linear movement to drive rod 270 which, in turn, moves jaw members 280 and 282 toward and away from each other.

Seating the generally rounded head 239 between clevis flanges 249a and 249b enables the user to utilize the rotating assembly 223 effectively without interfering with the linear movement of the piston 238.

The end effector assembly 222 includes first jaw 280, second jaw 282 and an electrically insulating yoke 284 disposed therebetween. Preferably, jaw member 280 and jaw member 282 are movable from an open position to a closed position by movement of the handle assembly 218 as described above. It is contemplated that either both or one of the jaw members 280 and 282 can be movable relative to one another. First jaw member 280 has a first flange 281 which extends therefrom and a cam slot 86 located therethrough. Likewise, second jaw 282 has a second flange 283 which extends therefrom and a cam slot 288 located therethrough.

The end effector assembly 222 also includes an outer nose portion 294 and an inner nose portion 296 which engage jaw members 282 and 280, respectively. A first pivot 305 is located on outer nose portion 294 and is dimensioned to engage a corresponding pivot hole 289 located on flange 283. A second pivot 303 is located on inner nose portion 296 and is dimensioned to engage a corresponding pivot hole 287 located on flange 281. The center of rotation for first jaw member 280 is at a first pivot hole 287 and the center of rotation for second jaw member 282 is at a second pivot hole 289. Preferably, each nose portion 294 and 296 is made from an electrically conductive material and transmits electrosurgical energy to a respective jaw member 282 and 280 as described in more detail below.

As mentioned above with respect to FIG. 13, electrosurgical energy is transmitted from the electrosurgical generator to an connector assembly 315 which includes the PC board 258 which converts the energy into first and second poles. A pair of terminal clips 264a and 264b are connected to PC board 258 and transfer the first and second poles of alternating potential, respectively, to the drive rod assembly 211. Clip 264a connects to shaft 212 and conducts the first pole to jaw member 282 and clip 264b connects to piston 238 which is, in turn, connected to drive rod 270. The second pole is conducted along drive rod 270 to jaw member 280. Both the drive rod 270 and the shaft 212 are made from an electrically conductive material and preferably an insulation sleeve 275 is disposed between drive rod 270 and shaft 212 to prevent the forceps 210 from short circuiting.

As best seen in FIG. 14, the inner nose portion 296 is electrically connected with drive rod 270 and the outer nose portion 294 is electrically connected to shaft 212. The inner and outer nose portions 296 and 294 capture yoke 284 along with flanges 283 and 281. Yoke 284 moves axially along axis "A" in a space between inner and outer portions 296 and 294 and a spacer stake 319 maintains the separation of the nose portions 296 and 294 at their distal ends. Stake 319 is dimensioned to engage and lock the inner and outer nose portions 296 and 294 together, which, in turn locks jaw members 280 and 282 atop yoke 284. In some cases it may be preferable to dimension stake 319 such that stake 319 acts as a stop member and controls the gap distance between the opposing jaw members 280 and 282 relative to one another. In this case, stake 319 is formed from an electrically insulative material such as plastic. The nose portions 294 and 296 provide lateral support for the flanges 281 and 283 and help ensure that detents 290 and 292 remain within cam slots 286 and 288, respectively.

End effector assembly. 222 also includes an inner insulator 302 and an outer insulator 300 for maintaining electrical insulation between poles. Outer insulator 300 insulates outer nose portion 294 from inner nose portion 296 and drive rod 270 which conduct the second pole of electrical energy. Inner insulator 302 insulates inner nose portion 296 from outer nose portion 294 and shaft 212 which conduct the first pole of electrical energy. In this manner, outer nose portion 294 can provide electrical continuity between shaft 212 and jaw member 282, while inner nose portion 296 can provide electrical continuity between drive rod 270 and jaw member 280.

Preferably, a spring contact 298 is utilized to maintain the electrical connection between drive rod 270 and inner nose portion 296 during axial motion of the drive rod 270. A donut-shaped spacer 308 can also be utilized to assure linear motion of the drive rod 270 within sleeve 275 and to prevent accidental short circuiting of the forceps 210.

Referring back to FIG. 14, yoke 284 is preferably formed from an electrically insulative material such as plastic. A first side 291 of yoke 284 faces first flange 281 and a second side 293 of yoke 284 faces second flange 283. When yoke 84 is positioned between flanges 281 and 283, yoke 284 electrically insulates first jaw member 80 from second jaw member 282. In this manner, bipolar electrosurgical current can be conducted through tissue 350 which is grasped between jaws 280 and 282 without flanges 281 and 283 short circuiting.

In order to achieve a desired gap range (e.g., about 0.001 to about 0.006 inches) and apply a desired force to seal the tissue, at least one jaw member 280 and/or 282 includes a stop member 339 which limits the movement of the two opposing jaw members 280 and 282 relative to one another. As explained above, in some cases it may be preferable to dimension stake 319 such that it acts like a stop member and limits the movement of the two opposing jaw members 280 and 282 relative to one another. Preferably, stop member 339 and/or stake 319 is made from an insulative material and is dimensioned to limit opposing movement of the jaw members 280 and 282 to within the above gap range.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16 and 18 is required to deflect the electrodes in the same plane.

Although it is preferable to vertically align electrodes 110 and 120, in some cases it may be preferable to offset the opposing electrodes 110 and 120 relative to one another either longitudinally or transversely to suit a particular purpose.

Although it is preferable that the electrode assembly 21 include housing 71 and cover plate 80 to engage mechanical forceps 20 therebetween, in some cases it may be preferable to manufacture the disposable electrode assembly 21 such that only one piece, e.g., housing 71 is required to engage mechanical forceps 20.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A removable electrode assembly for use with a forceps having opposing end effectors and a handle for effecting relative movement of the end effectors with respect to one another, the electrode assembly comprising:
   a housing having at least one portion which is removably engageable with at least a portion of the forceps;
   a pair of electrodes having opposing tissue sealing surfaces, said electrodes being removably engageable with the end effectors of the forceps such that the tissue sealing surfaces are disposed in opposing relation to one another, said electrodes being adapted for connection to a source of electrosurgical energy; and
   at least one stop member for controlling the distance between the opposing tissue sealing surfaces such that upon electrosurgical activation, tissue held between the tissue sealing surfaces seals into a fused mass.

2. A removable electrode assembly according to claim 1 wherein each of the electrodes includes an electrically conductive sealing surface and an insulating substrate.

3. A removable electrode assembly according to claim 2 wherein the stop member is attached to the insulating substrate.

4. A removable electrode assembly according to claim 1 wherein the distal end of the housing is bifurcated forming two prongs and each of the electrodes is attached to one of the prongs.

5. A removable electrode assembly according to claim 4 wherein the prongs of the housing are movable relative to one another to facilitate engagement of the electrodes with the end effectors of the forceps.

6. A removable electrode assembly according to claim 5 wherein the insulating substrate of each of the electrodes includes at least one mechanical interface for engaging a complimentary mechanical interface disposed on the corresponding end effector of the forceps.

7. A removable electrode assembly according to claim 6 wherein the mechanical interface of at least one of the substrates includes at least one detent and the mechanical interface of the corresponding end effector includes at least one complimentary socket for receiving the detent.

8. A removable electrode assembly according to claim 6 wherein the substrate of at least one of the electrodes includes at least one guide pin and the corresponding end effector includes at least one complimentary aperture for receiving the guide pin.

9. A removable electrode assembly according to claim 1 wherein the stop member is attached to at least one of the end effectors.

10. A removable electrode assembly according to claim 1 wherein the stop member is attached to at least one of the electrodes.

11. A removable electrode assembly according to claim 1 wherein the electrodes are tapered.

12. A removable electrode assembly according to claim 1 wherein each of the electrodes includes an electrical connector for coupling to a wire.

13. A removable electrode assembly according to claim 1 wherein the housing is removably engageable with the handle of the forceps.

14. A removable electrode assembly according to claim 1 further comprising a cover plate which is removably engageable with the housing.

15. A removable electrode assembly according to claim 1 wherein the housing includes a bifurcated distal end which forms two prongs and each electrode is removably attachable to one of the prongs.

16. A removable electrode assembly according to claim 15 wherein the prongs of the housing are movable relative to one another to facilitate engagement of the electrodes with the end effectors of the forceps.

17. A removable electrode assembly according to claim 1 further comprising at least one ratchet which engages at least one complementary mechanical interface to maintain a desired closure force between opposing electrodes.

18. A removable electrode assembly according to claim 1 further comprising a pair of opposing ratchets which interlock in at least one position for maintaining a desired closure force between opposing electrodes.

19. A removable electrode assembly according to claim 1 wherein the stop member maintains a gap distance between opposing tissue sealing surfaces in the range of about 0.001 inches to about 0.006 inches.

20. A removable electrode assembly according to claim 16 wherein the gap distance is in the range of about 0.002 inches to about 0.005 inches.

* * * * *